United States Patent [19]
Siebenhaar et al.

[11] Patent Number: 5,902,909
[45] Date of Patent: May 11, 1999

[54] INTERMEDIATES

[75] Inventors: Bernd Siebenhaar, Kandern, Germany; Bruno Casagrande, Münchenstein, Switzerland; Victor Eliu, Lörrach, Germany

[73] Assignee: Ciba Specialty Chemicals Corporation, Tarrytown, N.Y.

[21] Appl. No.: 08/994,220

[22] Filed: Dec. 19, 1997

[30]     Foreign Application Priority Data

Dec. 20, 1996  [GB]  United Kingdom ............ 9626514

[51] Int. Cl.⁶ .......................... C07C 33/38; C07C 29/60
[52] U.S. Cl. ......................... 568/813; 562/74; 564/291; 564/292; 568/643; 568/812; 585/435
[58] Field of Search ............... 562/74; 564/291, 564/292; 568/643, 812, 813; 585/435

[56]     References Cited

U.S. PATENT DOCUMENTS 2,465,486   3/1949   Rosenthal .............................. 260/669

FOREIGN PATENT DOCUMENTS 0 059 687   9/1982   European Pat. Off. .

OTHER PUBLICATIONS

Derwent Abst. 96–094135.

*Primary Examiner*—Peter O'Sullivan
*Attorney, Agent, or Firm*—Kevin T. Mansfield

[57]     ABSTRACT

The present invention provides compounds having the formula:

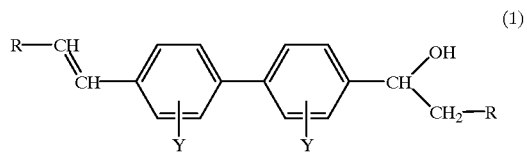

(1)

in which R is hydrogen or $C_1$–$C_4$alkyl, preferably hydrogen and Y is hydrogen, $C_1$–$C_4$alkyl, $C_1$–$C_4$alkoxy, $CF_3$, halogen (F, Cl, Br or I) or $SO_3M$ in which M is H, Na, K, Ca, Mg, ammonium, mono-, di-, tri- or tetra-$C_1$–$C_4$alkylammonium, mono-, di- or tri-hydroxyalkylammonium or ammonium that is di- or tri-substituted with a mixture of $C_1$–$C_4$alkyl and $C_1$–$C_4$hydroxyalkyl groups; a process for their production; and their use as intermediates in the production of asymmetric or symmetric fluorescent whitening agents.

25 Claims, No Drawings

INTERMEDIATES

The present invention relates to new compounds which are useful as intermediates for the production of fluorescent whitening agents and to a process for their production.

In U.S. Pat. No. 2,465,486, a process is described for the production of 4,4'-divinyl-biphenyl. This process comprises dehydrating 4,4'-di-(α-hydroxyethyl)-biphenyl in the presence of a dehydrating agent. The reaction is preferably conducted in an atmosphere of inert gas, at reduced pressure and at elevated temperature. The gaseous 4,4'-divinyl-biphenyl so obtained is chilled to convert it to the solid state.

A further known process for the production of 4,4'-divinyl-biphenyl is that described in JP 08003079. In this process, 4,4'-diethyl-biphenyl is contacted with a dehydrogenation catalyst in the presence of steam; a cooling medium is rapidly added to the gaseous reaction product containing 4,4'-divinyl-biphenyl; and a solution or dispersion containing the 4,4'-divinyl-biphenyl is formed.

The compound 4,4'-divinyl-biphenyl is known for use as a starting material for the production of copolymers with other monomers such as styrene. It is also possible to use 4,4'-divinyl-biphenyl as a starting material for certain fluorescent whitening agents. Thus, 4,4'-divinyl-biphenyl may be reacted, in the presence of a palladium compound, according to the Heck reaction, with diazo compounds to form distyryl-diaryl fluorescent whitening agents. If so used in the Heck reaction, however, there would be obtained only the corresponding symmetrical distyryl-diaryl fluorescent whitening agents.

The present invention provides, as a first aspect, a new class of vinyl-biphenyl compounds which are useful for the production of asymmetrical or symmetrical distyryl-diaryl fluorescent whitening agents.

Accordingly, the present invention provides compounds having the formula:

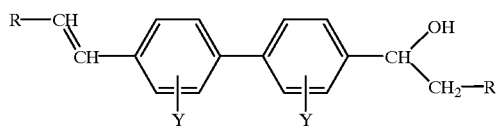
(1)

in which R is hydrogen or $C_1$–$C_4$alkyl, preferably hydrogen, and Y is hydrogen, $C_1$–$C_4$alkyl, $C_1$–$C_4$alkoxy, $CF_3$, halogen (F, Cl, Br or I) or $SO_3M$ in which M is hydrogen, Na, K, Ca, Mg, ammonium, mono-, di-, tri- or tetra-$C_1$–$C_4$alkylammonium, mono-, di- or tri-hydroxyalkylammonium or ammonium that is di- or tri-substituted with a mixture of $C_1$–$C_4$alkyl and $C_1$–$C_4$hydroxyalkyl groups. Preferably Y is hydrogen.

The preferred compound of formula (1) is 4-vinyl-4'-α-hydroxyethyl-biphenyl.

The present invention also provides a process for the production of a compound of formula (1), comprising partially dehydrating a compound having the formula (2):

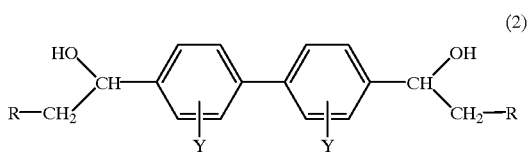
(2)

In which R and Y have their previous significance, at a temperature in the range of from 140 to 260° C., preferably in the range of from 180 to 220° C., in a high-boiling inert solvent.

The solvent used is preferably a polyalkylene glycol or a di-alkyl ether thereof, preferably a polyethylene glycol or a dimethyl ether thereof, especially diethylene glycol or triethylene glycol-dimethyl ether. If an acid-free solvent such as triethylene glycol-dimethyl ether is used, then a minor amount of an acidic compound such as p-toluene sulfonic acid is preferably present during the partial dehydation process according to the invention.

The partial dehydation process according to the second aspect of the invention is preferably conducted at normal pressure and in the presence of a effective amount of a compound which is an inhibitor of the polymerisation of styrene monomers. Examples of such polymerisation inhibitors include quinones, hindered phenols and amines. The preferred polymerisation inhibitor is tert.-butylpyrocatechol.

At dehydration temperatures above 200° C., the product of formula (1) begins to dehydrate to form 4,4'-divinyl-biphenyl. Accordingly, the reaction temperature used in the partial dehydation process according to the invention is preferably held in the range of from 180 to 220° C. and the content of the reaction mixture is monitored, and the reaction is stopped as soon as the optimal amount of the product of formula (2) is detected in the reaction mixture.

In addition to the partial dehydration process according to the present invention for the production of a compound of formula (1), other possible routes are available for obtaining a compound of formula (1). The various routes are summarised in the following scheme:

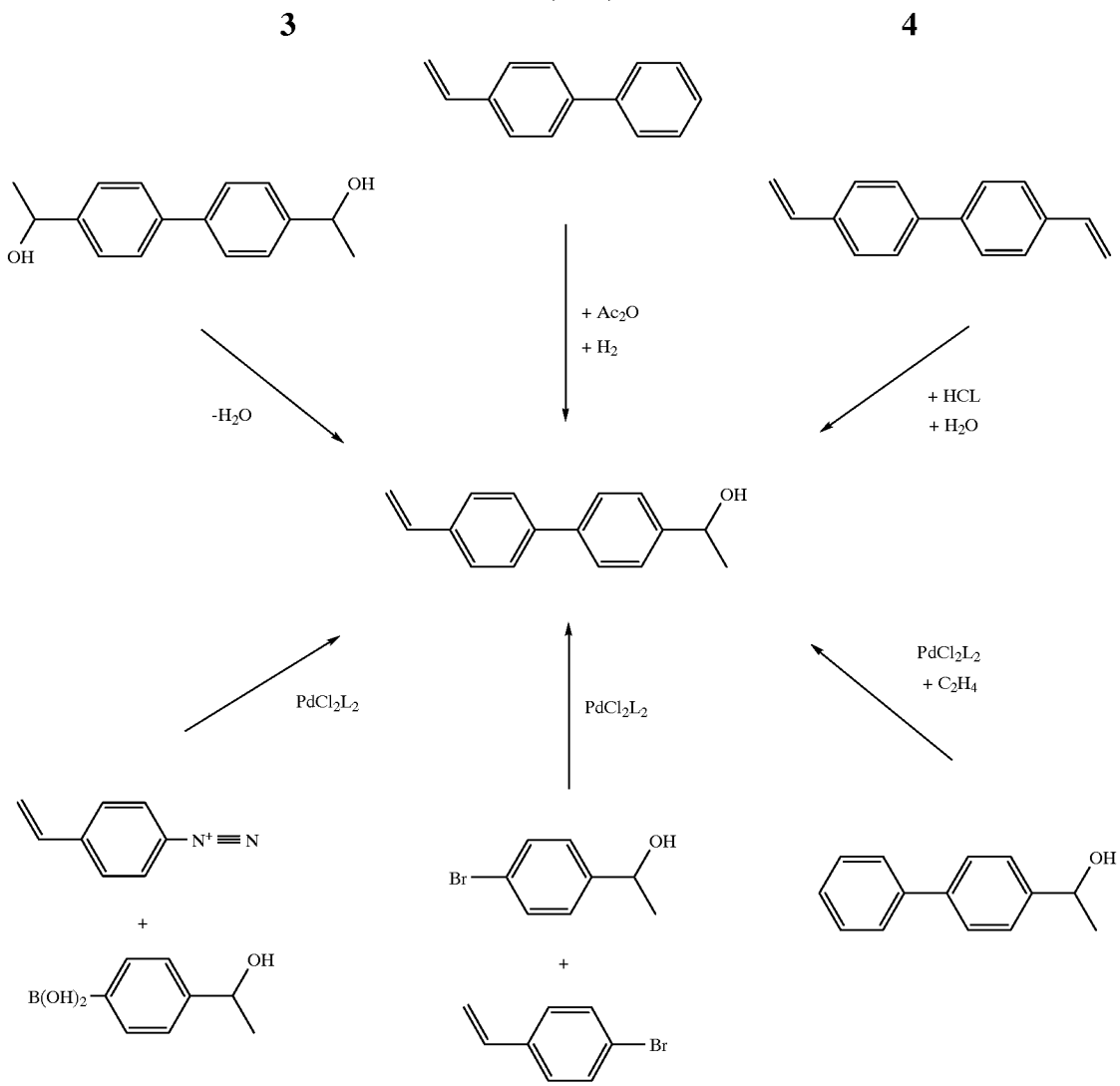

As a third aspect of the present invention, there is provided a process for the production of a compound having the formula:

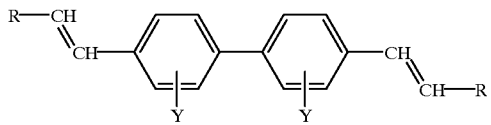

(3)

in which R and Y have their previous significance, comprising dehydrating a compound having the formula (1), at a temperature in the range of from 140 to 260° C., preferably in the range of from 180 to 220° C., in a high-boiling inert solvent.

The solvent used is preferably a polyalkylene glycol or an di-alkyl ether thereof, preferably a polyethylene glycol or a dimethyl ether thereof, especially diethylene glycol or triethylene glycol-dimethyl ether. If an acid-free solvent such as triethylene glycol-dimethyl ether is used, then a minor amount of an acidic compound such as p-toluene sulfonic acid is preferably present during the partial dehydation process according to the invention.

The dehydation process according to the third aspect of the present invention is preferably conducted at normal pressure and in the presence of a effective amount of a compound which is an inhibitor of the polymerisation of styrene monomers. Examples of such polymerisation inhibitors include quinones, hindered phenols and amines. The preferred polymerisation inhibitor is tert.-butylpyrocatechol.

The preferred starting material of formula (2) is 4-vinyl-4'-α-hydroxyethyl-biphenyl which is dehydrated according to the process of the third aspect of the present invention to produce 4,4'-divinyl-biphenyl.

A fourth aspect of the present invention comprises a process for the production of asymmetric or symmetric compounds having the formula:

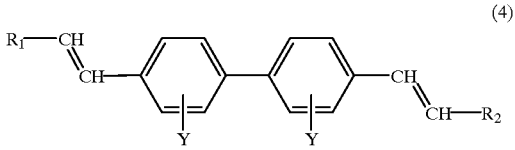

(4)

in which Y has its previous significance and $R_1$ and $R_2$ are the same or different and each is a phenyl group, optionally substituted with one or more groups of formula $SO_3M$ in which M has its previous significance, which process comprises:

a) reacting a compound having the formula (1), in the presence of a palladium compound, with a diazonium compound having the formula $R_1$—$N_2X^\ominus$ in which $X^\ominus$ is an anion, to produce a compound having the formula;

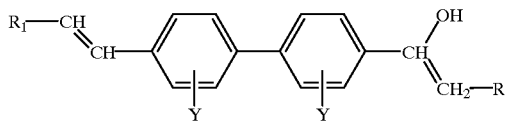

(5)

in which Y, R and $R_1$ have their previous significance;

b) dehydrating the compound having the formula (5), at a temperature in the range of from 140 to 260° C., preferably in the range of from 180 to 220° C., in a high-boiling inert solvent to produce a compound having the formula;

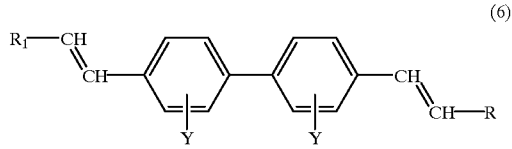

(6)

in which Y, R and $R_1$ have their previous significance; and c) reacting a compound having the formula (6), under the conditions of the Heck reaction, with a diazonium compound having the formula $R_2$—$N_2X^\ominus$ in which $R_2$ and $X^\ominus$ have their previous significance, to produce a compound having the formula (4).

Step b) of the process, the dehydration of the compound of formula (5) to the compound of formula (6), is conveniently conducted according to the dehydration procedure described in relation to the process for the production of a compound of formula (3), comprising dehydrating a compound having the formula(1).

The reaction of a compound having the formula (1) with a diazonium compound having the formula $R_1$—$N_2X^\ominus$, and the reaction of a compound having the formula (6) with a diazonium compound having the formula $R_2$—$N_2X^\ominus$, viz. steps a) and c) of the process, are each conducted under the conditions of the Heck reaction, namely in the presence of a palladium compound, as catalyst. The reaction is conducted in an organic solvent such as water, an aliphatic alcohol or an aliphatic acid.

Examples of palladium compound catalysts include inorganic palladium salts such as the chloride, bromide, iodide, nitrate, sulfate, acetate or propionate, and mixtures thereof. The palladium compound may also be used in the form of a complex. Examples of suitable complex formers include alkyl nitrites, such as $C_1$–$C_4$alkylnitriles, aryl nitrites such as benzonitrile, phosphites such as triphenyl phosphite, triaryl phosphanes such as triphenyl phosphane or the mono-, di- or tri-sodium salt thereof, bis(diarylphosphane)-alkanes such as bis(diarylphosphane)-methane, -ethane, -propane or -butane, trihetarylphosphanes such as trifurylphosphane and bis(dibenzalacetone). The organic complex formers may be substituted with one or more water-solubilising groups such as sulfo groups or carboxyl groups. The preferred palladium compound catalyst is palladium[bis(dibenzalacetone)]$_2$.

If the Heck reactions are effected in water, as solvent, preferably the palladium compound catalyst used contains one or more water-solubilising groups such as sulfo groups or carboxyl groups.

Preferably, however, the reaction steps a) and c) are conducted in an organic solvent, especially in a $C_1$–$C_{12}$alcohol or in a $C_1$–$C_4$alkanoic acid. Examples of such $C_1$–$C_{12}$alcohols include methanol, ethanol, n-propanol, iso-propanol, t-butyl alcohol, n-pentanol, n-hexanol, n-octanol, n-decanol and n-dodecanol. $C_1$–$C_4$alkanoic acids which may be used include formic acid, acetic acid, propionic acid and n-butyric acid.

The palladium compound catalyst is preferably used in an amount of 0.001 to 5 mole percent, more preferably 0.005 to 0.5 mole percent, based on the reactant of formula (1) or (6), respectively. The reaction temperature in steps a) and c) preferably ranges from 0 to 100° C., especially from 10 to 80° C.

After completion of step a) or c), the palladium catalyst is preferably recovered for re-use, by methods which are well-known.

The diazonium compounds having the formula $R_1$—$N_2X^\ominus$ or $R_2$—$N_2X^\ominus$ in which $R_1$, $R_2$ and $X^\ominus$ have their previous significance, used as respective reactants in steps a) and c), are known compounds and may be produced by methods known per se.

For example, the said diazonium compounds may be produced by reacting the corresponding amines of formula $R_1$—$NH_2$ or $R_2$—$NH_2$ with an alkali metal nitrite or with an alkyl nitrite in the presence an acid in aqueous or in organic solution. If the diazotisation is conducted in organic solution, it is preferred that the water, produced as a by-product of the diazotisation reaction, is removed as it is formed. The removal of such water may be conveniently conducted by effecting the diazotisation in the presence of water-binding materials such as acetic anhydride, sodium sulfate, calcium chloride or molecular sieves.

The compounds of formula (5) are new compounds per se and, as such, form a further aspect of the present invention.

The following Examples further illustrate the present invention. Parts and percentages shown therein are by weight unless otherwise stated.

EXAMPLE 1

15 g. 4,4'-di-($\alpha$-hydroxyethyl)-biphenyl 135 g. triethyleneglycol-dimethylether 0.3 g. tert.-butylpyrocatechol and 27 mg. toluene-4-sulfonic acid monohydrate are placed in a 500 ml. 3-necked flask. The contents of the flask are heated, with stirring under an atmosphere of argon. When the reaction temperature reaches 90° C., the 4,4'-di-($\alpha$-hydroxyethyl)-biphenyl starting material is dissolved and the reaction solution is clear. The conversion of 4-vinyl-4'-$\alpha$-hydroxyethyl-biphenyl to 4,4'-divinyl-biphenyl commences as the reaction temperature reaches 180° C. and the conversion continues until the boiling point (224–227° C.) of the triethyleneglycol-dimethylether is reached. The reaction mixture is held at the reflux temperature until a white turbidity forms in the reaction mixture (after about 50 minutes). At this point, the reaction is stopped by adding a base and by applying rapid cooling. The reaction mixture has the following composition:

50–55% 4,4'-divinyl-biphenyl

40–45% 4-vinyl-4'-$\alpha$-hydroxyethyl-biphenyl

2–5% 4,4'-di-($\alpha$-hydroxyethyl)-biphenyl and

0–5% by-products.

The cooled reaction solution is poured slowly, with stirring, into 2 liters of deionised water containing 100 mg. of tert.-butylpyrocatechol. The reaction products are precipitated and are filtered off. The separated precipitate is washed with 2 liters of deionised water containing 100 mg. of tert.-butylpyrocatechol and re-filtered. The moist filter-cake is then dried at 20° C. under vacuum for 3 days. The two main products, 4,4'-divinyl-biphenyl and 4-vinyl-4'-α-hydroxyethyl-biphenyl, are separated from one another on a silica column using a weakly basic solvent.

EXAMPLE 2

15 g. 4,4'-di-(α-hydroxyethyl)-biphenyl 135 g. triethyleneglycol-dimethylether 0.3 g. tert.-butylpyrocatechol and 27 mg. toluene-4-sulfonic acid monohydrate are placed in a 500 ml. 3-necked flask. The contents of the flask are heated, with stirring under an atmosphere of nitrogen. When the reaction temperature reaches 90° C., the 4,4'-di-(α-hydroxyethyl)-biphenyl starting material is dissolved and the reaction solution is clear. The conversion of 4-vinyl-4'-α-hydroxyethyl-biphenyl to 4,4'-divinyl-biphenyl commences as the reaction temperature reaches 180° C. and the conversion continues until the boiling point (224–227° C.) of the triethyleneglycol-dimethylether is reached. The reaction mixture is held at the reflux temperature and after about 30 minutes the reaction is stopped by adding a base and by applying rapid cooling. The reaction mixture has the following composition:

10–17% 4,4'-divinyl-biphenyl

35–40% 4-vinyl-4'-α-hydroxyethyl-biphenyl

18–20% 4,4'-di-(α-hydroxyethyl)-biphenyl and

0–5% by-products.

The cooled reaction solution is then worked up in the manner described in Example 1.

EXAMPLE 3

Production of an Asymmetric Fluorescent Whitening Agent.

A) Synthesis of the First Diazonium Compound

Into 150 g of anhydrous acetic acid there are stirred 38 g of 3-amino-benzene sulfonic acid (100%) and 13.8 g of concentrated sulfuric acid (96%) and the mixture is cooled externally to 5–10° C. At the same temperature, over 1 hour, 31.7 g of of a 50% aqueous solution of sodium nitrite are added, dropwise, and the whole is stirred for a further hour, the temperature being held below 10° C. by means of cooling. Finally, the nitrite excess is determined and the necessary amount of 3-aminobenzene sulfonic acid is added to remove the excess.

B) Reaction of the First Diazonium Compound with 4-Vinyl-4'-α-Hydroxyethyl-Biphenyl 200 g of acetic anhydride are added, dropwise, over 3 hours, to the diazo suspension obtained in step A), whereupon a weakly exothermic reaction takes place. The reaction mixture is stirred for 1 hour, 32.8 g of anhydrous sodium acetate are added, the whole is stirred well, treated with 1 g of palladium[bis(dibenzalacetone)]₂ and, after 5 minutes, 45 g of 4-vinyl-4'-α-hydroxyethyl-biphenyl and 0.05 g of tert-butyl-pyrocatechol are added. The reaction mixture is stirred at 18–20° C. for 10 hours, heated to 40° C. and held at this temperature for a further 5 hours.

The acetic acid is removed by distillation under vacuum, the melt so obtained is made up to 400 mls volume by adding water and heated to 90° C. Crystallisation of the reaction product from the solution is induced by cooling the solution to 15° C. using a ramp. Finally, the product which crystallises out is separated by filtration, washed and dried under vacuum. In this way, 83 g of the compound of formula:

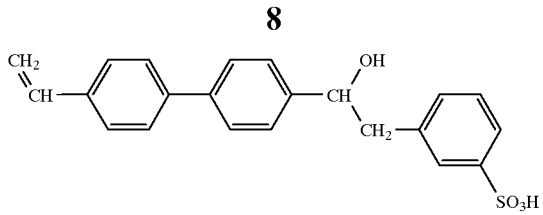

are obtained which represents a yield of 83%, based on the amount of 4-vinyl-4'-α-hydroxyethyl-biphenyl used.

C) Dehydration Step

The dried product from step B) is stirred into 750 g of triethylene glycol dimethylether and 1 g of tert-butyl-pyrocatechol and 0.2 g of toluene-4-sulfonic acid are added. The reaction mixture is then heated, with stirring. The dehydration begins when the reaction mixture reaches a temperature above 180° C. and continues until the reaction mixture attains the boiling point (224–227° C.) of the triethylene glycol dimethylether. The reaction mixture is held at the reflux temperature for 2 hours, then it is cooled and neutralised by adding a base to give the product of formula:

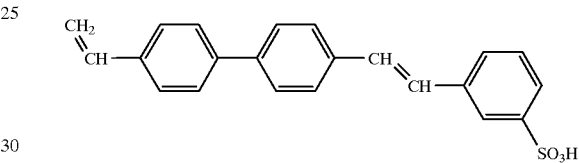

D) Synthesis of the Second Diazonium Compound

Into 150 g of triethylene glycol dimethylether there are stirred 29.4 g of 2-amino-benzenesulfonic acid (100%; 32.6 g of technical grade product) and 7 g of water, and the mixture is cooled externally to 5–10° C. At the same temperature, over 1 hour, 21.0 g of amyl nitrite are added, dropwise, and the reaction mixture is stirred for a further 2 hours. Finally, the nitrite excess is determined and the necessary amount of 2-aminobenzene sulfonic acid is added to remove the excess.

E) Reaction of the Second Diazonium Compound with 4-Vinyl-4'(β-Styryl-3-Sulfonic Acid) Biphenyl 20 g of acetic anhydride are added, dropwise, over 2 hours, to the diazo suspension obtained in step D), whereupon a weakly exothermic reaction takes place. The reaction mixture is stirred for 1 hour, 32.8 g of anhydrous sodium acetate are added, the whole is stirred well, treated with 1 g of palladium[bis(dibenzalacetone)]₂ and, after 5 minutes, the reaction mixture is combined with that from step C). The reaction mixture is stirred at 18–20° C. for 10 hours, heated to 40° C. and held at this temperature for a further 5 hours.

The volatile components, namely amyl alcohol, acetic acid and triethylene glycol dimethylether are removed by distillation under vacuum. The melt so obtained is made up to 300 mls volume by adding water and heated to 90° C. The insoluble components are separated by clarification. Crystallisation of the reaction product from the solution is induced by cooling the solution to 15° C. using a ramp. Finally, the product which crystallises out is separated by filtration, washed and dried under vacuum. In this way, 75 g of the compound of formula:

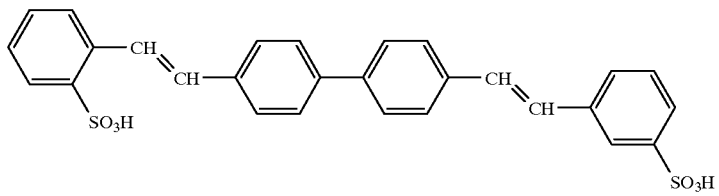

are obtained, representing a total yield of 66%, based on the weight of vinyl compound used.

We claim:

1. A compound having the formula:

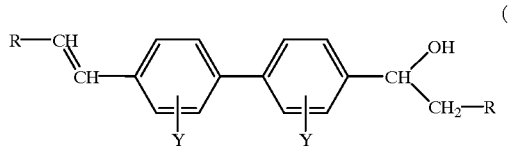
(1)

in which R is hydrogen or $C_1$–$C_4$alkyl and Y is hydrogen, $C_1$–$C_4$alkyl, $C_1$–$C_4$alkoxy, $CF_3$, halogen selected from the group consisting of F, Cl, Br or I or $SO_3M$ in which M is hydrogen, Na, K, Ca, Mg, ammonium, mono-, di-, tri- or tetra-$C_1$–$C_4$alkylammonium, mono-, di- or tri-hydroxyalkylammonium or ammonium that is di- or tri-substituted with a mixture of $C_1$–$C_4$alkyl and $C_1$–$C_4$hydroxyalkyl groups.

2. A compound according to claim 1 which is 4-vinyl-4'-α-hydroxyethyl-biphenyl.

3. A process for the production of a compound of formula (1), as defined in claim 1, comprising partially dehydrating a compound having the formula (2):

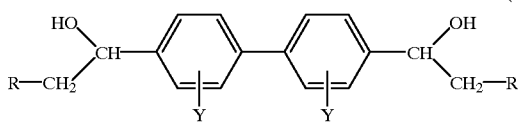
(2)

In which R is hydrogen or $C_1$–$C_4$alkyl and Y is hydrogen, $C_1$–$C_4$alkyl, $C_1$–$C_4$alkoxy, $CF_3$, halogen selected from the group consisting of F, Cl, Br or I or $SO_3M$ in which M is hydrogen, Na, K, Ca, Mg, ammonium, mono-, di-, tri- or tetra-$C_1$–$C_4$alkylammonium, mono-, di- or tri-hydroxyalkylammonium or ammonium that is di- or tri-substituted with a mixture of $C_1$–$C_4$alkyl and $C_1$–$C_4$hydroxyalkyl groups, at a temperature in the range of from 140 to 260° C. in a high-boiling inert solvent.

4. A process according to claim 3 in which the partial dehydration is conducted at a temperature in the range of from 180 to 220° C.

5. A process according to claim 3 in which the solvent is a polyalkylene glycol or a di-alkyl ether thereof.

6. A process according to claim 5 in which the polyalkylene glycol or a di-alkyl ether thereof is a polyethylene glycol or a dimethyl ether thereof.

7. A process according to claim 6 in which the polyethylene glycol or a dimethyl ether thereof is diethylene glycol or triethylene glycol-dimethyl ether.

8. A process according to claim 3 in which an acid-free solvent is used and a minor amount of an acidic compound is present during the partial dehydation process.

9. A process according to claim 8 in which the acid-free solvent is triethylene glycol-dimethyl ether and the acidic compound is p-toluene sulfonic acid.

10. A process according to claim 3 in which the partial dehydation process is conducted at normal pressure and in the presence of a effective amount of a compound which is an inhibitor of the polymerisation of styrene monomers.

11. A process according to claim 10 in which the polymerisation inhibitor is a quinone, a hindered phenol or an amine.

12. A process according to claim 11 in which the polymerisation inhibitor is tert.-butylpyrocatechol.

13. A process according to claim 3 in which the temperature is in the range of from 180 to 220° C. and the content of the reaction mixture is monitored, and the reaction is stopped as soon as the optimal amount of the product of formula (2) is detected in the reaction mixture.

14. A process for the production of a compound having the formula:

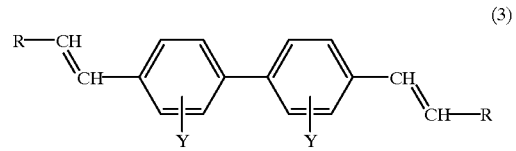
(3)

in which R is hydrogen or $C_1$–$C_4$alkyl and Y is hydrogen, $C_1$–$C_4$alkyl, $C_1$–$C_4$alkoxy, $CF_3$, halogen selected from the group consisting of F, Cl, Br or I or $SO_3M$ in which M is hydrogen, Na, K, Ca, Mg, ammonium, mono-, di-, tri- or tetra-$C_1$–$C_4$alkylammonium, mono-, di- or tri-hydroxyalkylammonium or ammonium that is di- or tri-substituted with a mixture of $C_1$–$C_4$alkyl and $C_1$–$C_4$hydroxyalkyl groups, comprising dehydrating a compound having the formula:

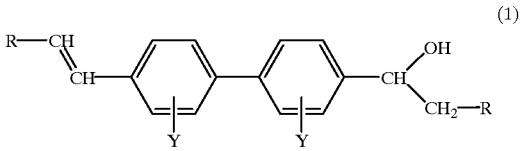
(1)

in which R and Y have their previous significance, at a temperature in the range of from 140 to 260° C. in a high-boiling inert solvent.

15. A process according to claim 14 in which the dehydration is conducted at a temperature in the range of from 180 to 220° C.

16. A process according to claim 14 in which the solvent is a polyalkylene glycol or a di-alkyl ether thereof.

17. A process according to claim 16 in which the polyalkylene glycol or a di-alkyl ether thereof is a polyethylene glycol or a dimethyl ether thereof.

18. A process according to claim 17 in which the polyethylene glycol or a dimethyl ether thereof is diethylene glycol or triethylene glycol-dimethyl ether.

19. A process according to claim 14 in which an acid-free solvent is used and a minor amount of an acidic compound is present during the partial dehydation process.

20. A process according to claim 19 in which the acid-free solvent is triethylene glycol-dimethyl ether and the acidic compound is p-toluene sulfonic acid.

21. A process according to claim 14 in which the partial dehydation process is conducted at normal pressure and in the presence of a effective amount of a compound which is an inhibitor of the polymerisation of styrene monomers.

22. A process according to claim 21 in which the polymerisation inhibitor is a quinone, a hindered phenol or an amine.

23. A process according to claim 22 in which the polymerisation inhibitor is tert.-butylpyrocatechol.

24. A process according to claim 14 in which starting material of formula (1) is 4-vinyl-4'-α-hydroxyethyl-biphenyl which is dehydrated to produce 4,4'-divinyl-biphenyl.

25. A compound having the formula:

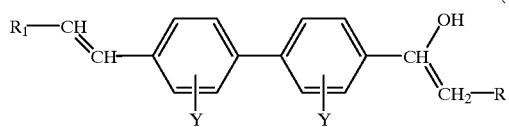

(5)

in which R is hydrogen or $C_1$–$C_4$alkyl, Y is hydrogen, $C_1$–$C_4$alkyl, $C_1$–$C_4$alkoxy, $CF_3$, halogen selected from the group consisting of F, Cl, Br or I or $SO_3M$ in which M is H, Na, K, Ca, Mg, ammonium, mono-, di-, tri- or tetra-$C_1$–$C_4$alkylammonium, mono-, di- or tri-hydroxyalkylammonium or ammonium that is di- or tri-substituted with a mixture of $C_1$–$C_4$alkyl and $C_1$–$C_4$hydroxyalkyl groups and $R_1$ is a phenyl group, optionally substituted with one or more groups of formula $SO_3M$ in which M has its previous significance.

* * * * *